United States Patent [19]

Huang et al.

[11] Patent Number: 5,132,433

[45] Date of Patent: Jul. 21, 1992

[54] PROCESS FOR THE PREPARATION OF CLAUSENAMIDE AND NEOCLAUSENAMIDE, AND DERIVATIVES THEREOF

[75] Inventors: Liang Huang; Geng-tao Liu, both of Beijing, China

[73] Assignees: Bayer Aktiengesellschaft, Leverkusen, Fed. Rep. of Germany; Chinese Academy of Medical Sciences, Beijing, China

[21] Appl. No.: 566,731

[22] Filed: Aug. 13, 1990

[30] Foreign Application Priority Data

Aug. 19, 1989 [DE] Fed. Rep. of Germany ....... 3927370

[51] Int. Cl.$^5$ .......................................... C07D 207/26
[52] U.S. Cl. .................................... 548/544; 548/534
[58] Field of Search ............................... 548/544, 534

[56] References Cited

FOREIGN PATENT DOCUMENTS

| 0222163 | 5/1987 | European Pat. Off. |
| 0244717 | 11/1987 | European Pat. Off. |
| 0362556 | 4/1990 | European Pat. Off. |
| 2811256 | 9/1978 | Fed. Rep. of Germany |
| 3431257 | 3/1986 | Fed. Rep. of Germany |
| 3537075 | 4/1987 | Fed. Rep. of Germany |
| 3616989 | 11/1987 | Fed. Rep. of Germany |

OTHER PUBLICATIONS

Journal of the American Chemical Society, vol. 107, 1985, pp. 1438-1439; S. Hanessian et al.: "A New Synthetic Strategy for the Penemas, Total Synthesis of [5R,6S, 8R]-6-[Hydroxyethyl]-2-[Hydroxymethyl]-Penem-3-Carboxylic Acid", p. 1439, left column, Compound 1.

Journal of Organic Chemistry, vol. 52, No. 19, Sep. 18, 1987, pp. 4352-4358; W. Hartwig, et al., "Diastereoselective and Enantioselective Total Synthesis of the Hepatoprotective Agent Clausenamide".

Chemical Abstracts, vol. 106, No. 19, May 11, 1987, Columbus, Oh., USA, M. Yang et al.: "Isolation and Structural Elucidation of Clausenamide from the Leaves of Clausena Iansium [Lour.] Skeels" p. 401; ref. No. 153109Z & Yaoxue Xueboa 1987, 22[1], 33-40.

Primary Examiner—David B. Springer
Attorney, Agent, or Firm—Sprung, Horn Kramer & Woods

[57] ABSTRACT

A process for the preparation of compound of the formula

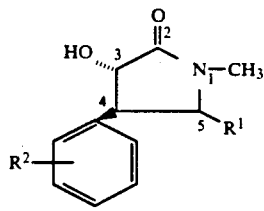

in which
$R^1$—represents

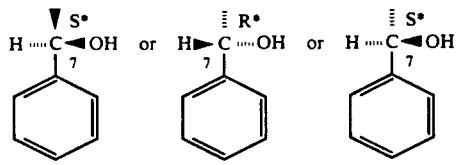

and
$R^2$—represents hydrogen, fluorine, chlorine or bromine. Comprising cyclizing compounds of the formula

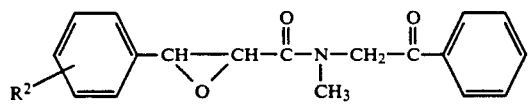

and, in a further step, either
a) reducing stereo-specifically to give compounds of the formula in which $R^1$ represents

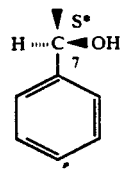

or
b), to give compounds of the formula in which $R^1$ represents

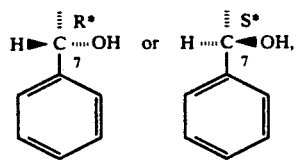

or by
c) forming compounds of the formula (Abstract continued on next page.)

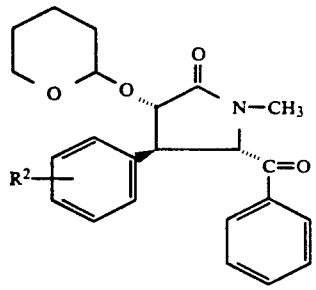
followed by stereoselective reduction to give compounds in which $R^1$ represents
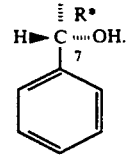
13 Claims, No Drawings

PROCESS FOR THE PREPARATION OF CLAUSENAMIDE AND NEOCLAUSENAMIDE, AND DERIVATIVES THEREOF

The invention relates to a process for the preparation of (±) 3(S*), 4(R*), 5(R*), 7(S*)-1-methyl-3-hydroxy-4-phenyl-5-(α-hydroxybenzyl)-pyrrolidin-2-one (clausenamide) and (±) 3(S*), 4(R*), 5(S*), 7(R*)-1-methyl-3-hydroxy-4-phenyl-5-(α-hydroxybenzyl)pyrrolidin-2-one (neoclausenamide), and of their derivatives.

Clausenamide, neoclausenamide, and some of their derivatives and processes for their preparation are already known [cf. DE-A1 3,616,989; J. Org. Chem. 52 (19), 4352–4358; Phytochemistry 28 (2), 445–450; DE-A1 3,632,589, DE-A1 3,537,075 and DE-A1 3,431,257]. It is also known that Clausena anicata, from the family of the Rutaceae, is used in certain parts of Africa as folk medicine [cf. J. Mester et al., Planta Medica 32, 81 (1977)]. It is likewise known that the crude extract of Clausena indica Oliv. has cardiovascular activity, and that two coumarin derivatives which have been isolated from Clausena pentaphalla (Roxb.) by thin-layer chromatography, namely clausmarin A and B, have spasmolytic activity [cf. Dhan Prakasheta et al., J. Chem. Soc. Chem. Commun. 1978, 281]. Furthermore, the aqueous extract from leaves of Clausena lansium (lour) Skeels is used in Chinese folk medicine as an effective means for protecting the liver and is administered against acute and chronic viral hepatitis.

From this extract, (±) 3(S*), 4(R ), 5(R*), 7(S*)-1-methyl-3-hydroxy-4-phenyl-5-(α-hydroxybenzyl)pyrrolidin-2-one (clausenamide) and (±) 3(S*), 4(R*), 5(S*), 7(R*)-1-methyl-3-hydroxy-4-phenyl-5-(α-hydroxybenzyl)pyrrolidin-2-one (neoclausenamide) were isolated as the main constituents.

In animal experiments, clausenamide shows an antiamnaesic effect as well as an effect which protects cerebral hypoxia while neoclausenamide shortens the sleeping time induced by barbiturates significantly. Moreover, in mice, clausenamide and neoclausenamide suppress the glutamine-pyruvate-transaminase serum level increased by carbon tetrachloride.

Further pharmacological studies now require larger amounts of clausenamide and neoclausenamide than can be obtained by the complicated extraction process. It was therefore necessary to provide a chemical process which facilitates the preparation of clausenamide and neoclausenamide as well as the formation of their derivatives. Furthermore, the novel chemical process was also intended to be distinguished by monitoring the stereoselectivity or, stereospecifically in the direction of the preferred isomers having the (3S*, 4R*, 5R*, 7S*) and (3S*, 4R*, 5S*, 7R*) configuration, to give considerably better yields than the processes which have already been published.

The present invention therefore relates to a process for the preparation of clausenamide, neoclausenamide and their derivatives of the general formula (I)

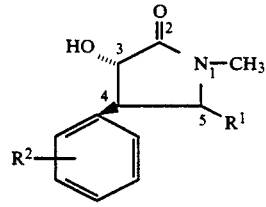

in which
R¹—represents the group of the formula

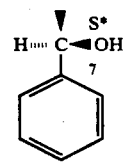

(clausenamide
3S*, 4R*,
5R*, 7S*), or

—represents the group of the formula

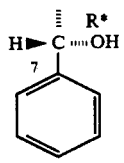

(neoclausenamide
3S*, 4R*, 5S*, 7R*), or

—represents the group of the formula

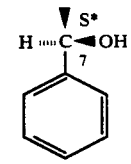

and
R²—represents hydrogen, fluorine, chlorine or bromine.

The compounds of the general formula (I) can be prepared by initially cyclizing compounds of the general formula (II)

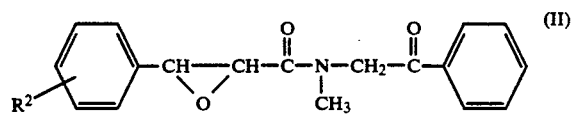

in which
R²—represents hydrogen, fluorine, chlorine or bromine, in inert organic solvents in the presence of a base, with the formation of the two isomers of the formulae (III) and (IV)

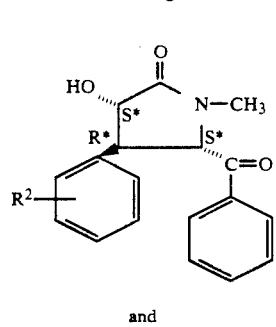

(III)

and

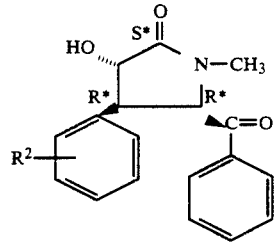

(IV)

in which
R² has the abovementioned meaning,
and, in a further step, either
(a) reducing compounds of the general formula (IV) stereo-specifically to give compounds of the general formula (I) in which R¹ represents the group of the formula

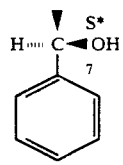

(clausenamide), or
(b), depending on the reaction conditions and the reducing agents chosen, by reducing compounds of the general formula (III) to give compounds of the general formula (I) in which R¹ represents the group of the formula

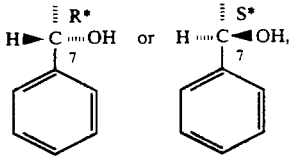

or by
(c) reacting compounds of the general formula (III) with 2,3-dihydropyran to give compounds of the general formula (V)

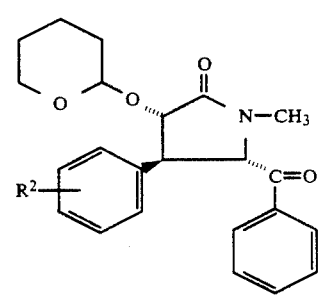

(V)

in which
R² has the abovementioned meaning, followed by stereoselective reduction to give compounds of the general formula (I) in which R¹ represents the group of the formula

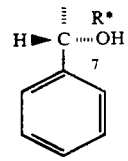

and, if appropriate, separating the isomers by a customary chromatographic method.

The process according to the invention can be illustrated by the following equation:

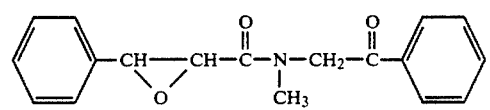

cyclization

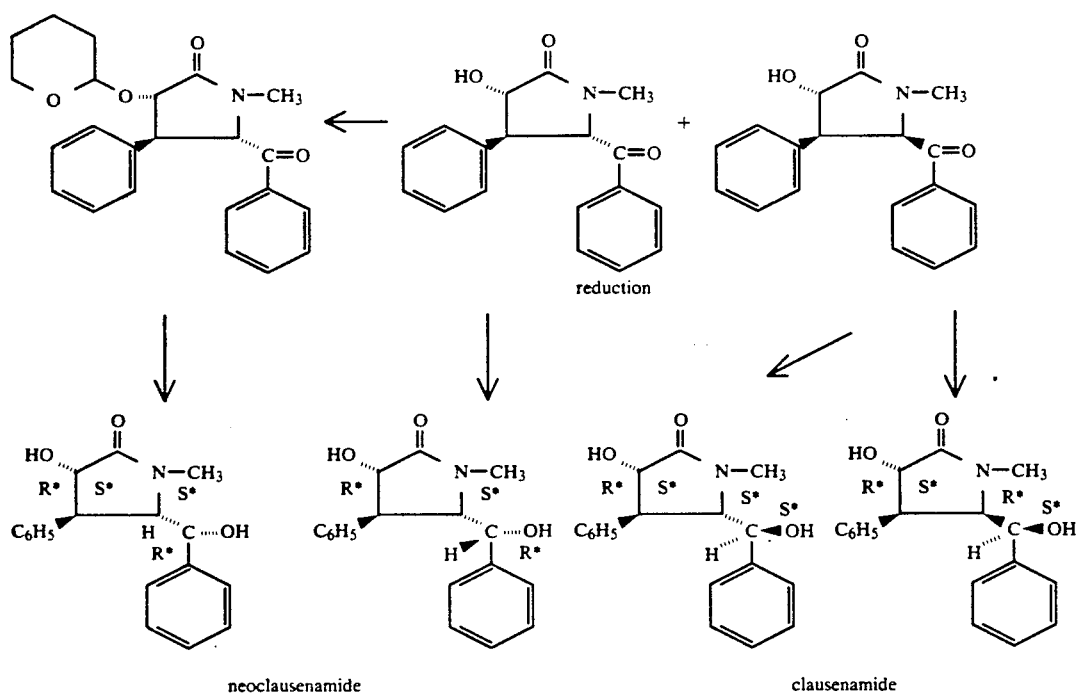

neoclausenamide            clausenamide

Suitable solvents for the cyclization are inert organic solvents, such as ethers, for example tetrahydrofuran, diethyl ether or dioxane, or alcohols, such as, for example, methanol or ethanol, or halogenated hydrocarbons, such as, for example, methylene chloride or carbon tetrachloride, or their mixtures, if appropriate also with water. Preferred solvents are tetrahydrofuran, methanol and methylene chloride.

Suitable bases for the cyclization are alkali metal alcoholates, alkali metal amides or alkali metal hydrides, such as, for example, sodium ethoxide, sodium methoxide, potassium butoxide, sodium butoxide or lithium butoxide, lithium hydroxide, sodium hydroxide or potassium hydroxide, sodium hydride, lithium diisopropylamide, butyllithium or ammonium hydroxides, such as, for example, tetramethylammonium hydroxide. Preferred bases are lithium diisopropylamide, sodium methoxide, lithium hydroxide or tetramethylammonium hydroxide.

Depending on the base and the reaction conditions, the formation of products of the compounds of the general formulae (III) and (IV) can be monitored. The abovementioned alkali metal alcoholates and alkali metal hydroxides in methanol have an overall favourable effect on the cyclization, while the compounds of the general formula (IV) are preferentially obtained under the conditions of a 2-phase-transfer reaction, for example with tetramethylammonium hydroxide as the base.

The reaction temperatures are between $-70°$ C. and $+40°$ C. The reaction is preferably carried out between $-65°$ C. and $+30°$ C.

For carrying out the cyclization, 1 to 5, preferably 1 to 2.5, moles of base are employed per mole of starting compound.

The cyclization step can be carried out under atmospheric pressure, but also under increased or reduced pressure In general, the cyclization step is carried out under atmospheric pressure.

The keto function is reduced to the hydroxyl function by means of the customary reducing agents, such as metallic hydrides, complex hydrides or with organic aluminium compounds. Preferred reducing agents are sodium borohydride, zinc borohydride, lithium tri-sec-butyl-borohydride or aluminium propoxide.

Suitable solvents for this purpose are all inert organic solvents which do not undergo changes under the reaction conditions. These preferably include halogenated hydrocarbons, such as methylene chloride, alcohols, such as methanol, ethanol, propanol or isopropanol, or ethers, such as diethyl ether, dioxane, tetrahydrofuran, glycol dimethyl ether or diethylene glycol dimethyl ether, or amides, such as hexamethylphosphoric triamide, or dimethylformamide, or acetic acid, or dimethoxyethane. It is also possible to use mixtures of the solvents mentioned. Catalysts which are used in the reduction are, in general, proton acids. These preferably include inorganic acids, such as, for example, hydrochloric acid or sulphuric acid, or organic carboxylic acids having 1-6C atoms, optionally substituted by fluorine, chlorine and/or bromine, such as, for example, acetic acid, trifluoroacetic acid, trichloroacetic acid or propionic acid, or sulphonic acids having $C_1$-$C_4$-alkyl radicals, or having aryl radicals, such as, for example, methanesulphonic acid, ethanesulphonic acid, benzenesulphonic acid or toluenesulphonic acid.

To destroy an excess of reducing agent, hydrogen peroxide or bases, such as sodium hydroxide or water, can be employed.

The reduction is carried out at a reaction temperature of $-10°$ C. to $+100°$ C., preferably at $0°$ C. to $+80°$ C.

The reduction can be carried out under atmospheric pressure, but also under increased or reduced pressure. In general, the reduction is carried out under atmospheric pressure.

In principle, it must be borne in mind that in the reduction of the C(7)-keto group to the C(7)-hydroxyl function in the compounds of the general formula (III)

and (IV), a further centre of chirality is formed and that therefore two diastereomers can be obtained.

By selecting the reducing agent, the reduction can be monitored stereospecifically, or the stereoselectivity can be increased For example, when the compounds of the general formula (IV) are reduced with sodium borohydride/tetrahydrofuran or sodium borohydride/methanol, the expected isomer of the configuration (3S*, 4R*, 5R*, 7S*) (clausenamide and derivatives) is obtained stereospecifically. While in the reduction of the ketones of the general formula (III) the product ratio of the resulting isomers can be monitored to a certain extent by the choice of the reaction conditions and the reducing agent, the conversion of the compounds of the general formula (III) to the compounds of the general formula (V) by protecting the hydroxyl function, for example by reaction with 2,3-dihydropyran, followed by reducing the latter with sodium borohydride/tetrahydrofuran or lithium tri-sec-butylborohydride, makes it possible to increase the stereo-selectivity in the direction of the isomer of the desired configuration (3S*, 4R*, 5R*, 7R*) (neoclausenamide and derivatives) by >90%.

The etherification with 2,3-dihydropyran is carried out in one of the abovementioned inert solvents, preferably in methylene chloride, in the presence of a catalyst, for example pyridinium p-toluenesulphate acid, at room temperature and atmospheric pressure.

The compounds of the general formula (II) are novel and can be prepared by

[A] initially converting compounds of the genearal formula

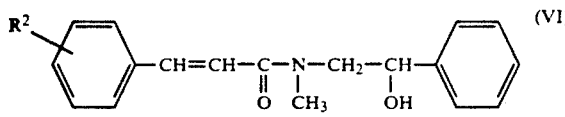

in which
R² has the abovementioned meaning, into compounds of the general formula (VII)

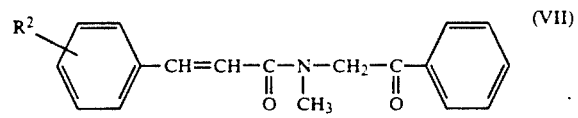

in which
R² has the abovementioned meaning, by oxidizing the hydroxyl group in a customary manner, and, in a second step, carrying out an epoxidization in a known manner, or by

[B] initially amidating compounds of the general formula (VIII)

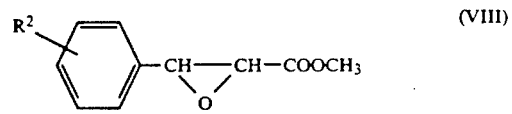

in which
R² has the abovementioned meaning, with the amine of the formula (IX)

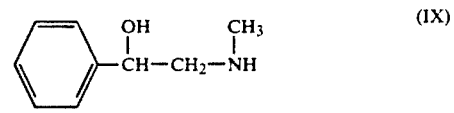

by a customary method, to give compounds of the general formula (X)

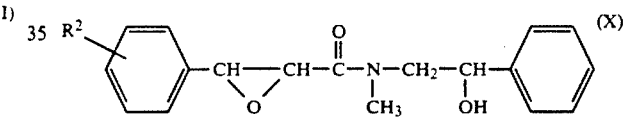

in which R² has the abovementioned meaning, and, in a further step, oxidizing the hydroxyl group in a known manner.

The course of the reaction can be illustrated by the following equation:

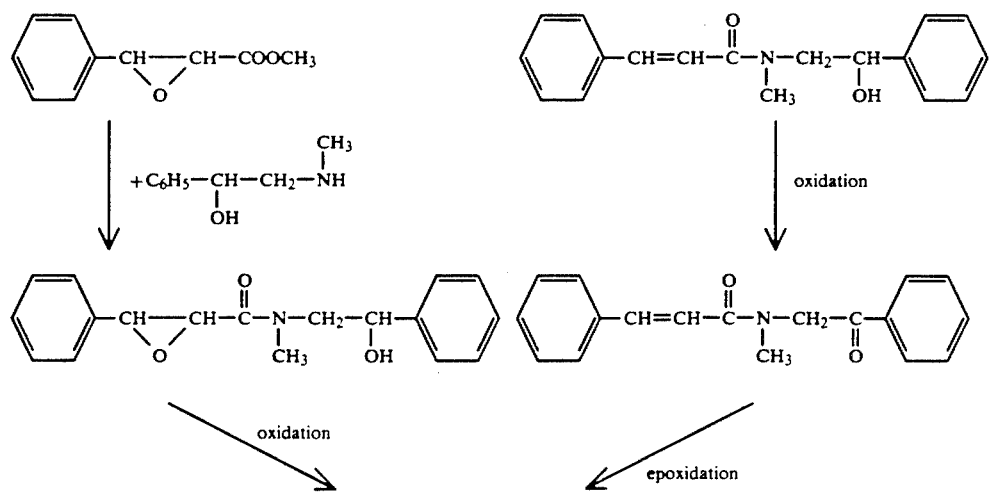

-continued

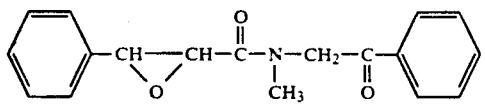

Suitable solvents for the oxidation of the hydroxyl group are the customary organic solvents which do not undergo changes under the reaction conditions. These preferably includes hydrocarbons, such as, for example, benzene, toluene, xylene, hexane, cyclohexane or mineral oil fractions, ethers, such as diethyl ether, tetrahydrofuran or dioxane, alcohols, such as, for example, methanol, ethanol or propanol, halogenated hydrocarbons, such as, for example, dichloromethane, trichloromethane, tetrachloromethane or 1,2-dichloroethane, glacial acetic acid, acetonitrile or hexamethylphosphoric triamide. Likewise, it is possible to use mixtures of the solvents mentioned.

Oxidizing agents which can be employed are organic or inorganic peroxo compounds, such as, for example, chloroperbenzoic or peroxyacetic acid, or inorganic oxides, such as, for example, chromium oxides or complex chromium oxides/pyridine. The preferred oxidizing agent is chromium oxide.

The reaction temperatures can be varied within a range of from 0° C. to +70° C. The process is preferably carried out at between +10° C. and +30° C.

The oxidations are carried out under atmospheric pressure.

When carrying out the oxidation, 1 to 10 moles, preferably 5 moles, of oxidizing agent are employed per mole of starting compound.

The epoxidization likewise proceeds in the inert solvents which have been mentioned in the case of the general oxidation. Preferred solvents in this case are carbon tetrachloride and methylene chloride.

Suitable oxidizing agents for the epoxidization are organic peracids, such as, for example, peroxyacetic acid or perbenzoic acid, or trifluoroacetic acid, or oxides of manganese, such as, for example, manganese dioxide. Preferred oxidizing agents are m-chloroperbenzoic acid and manganese dioxide.

The instructions given in the case of the general oxidation, concerning the amount of oxidizing agent, the reaction temperature, the pressure and the temperature, also hold true for the epoxidization reaction.

The amidation proceeds in one of the above-mentioned inert solvents, preferably in methanol.

Auxiliaries which can be employed are tertiary amines, such as, for example, 1,5-diazabicyclo(4.3.0)-non-5-ene or 1,8-diazabicyclo(5.4.0)undec-7-ene or dimethylaminopyridine.

The reaction temperatures can be varied between −30° C. and 0° C. The reaction is preferably carried out between −20° C. and −10° C.

The compounds of the general formula (VI) are known per se or can be prepared by known methods [cf. Indian J. Chem., Sect. B, 19B (12), 1075–1076].

The compounds of the general formula (VIII) are known per se or can be prepared by a customary method [cf. Beilstein, 18 (3), 4200].

The compounds of the general formula (IX) are known per se and can be prepared and employed by a customary method [cf. Helv. Chim. Acta 1978, 61 (6), 2237–2240].

Examples which may be mentioned are:

2-ethylamino-1-phenylethanol
2-methylamino-1-phenylethanol.

It must be considered as surprising that the process according to the invention gives good yields of the compounds of the correct configurations, such as clausenamide (3S*, 4R*, 5R*, 7S*) and neoclausenamide (3S*, 4R*, 5S*, 7R*) and their derivatives.

The compounds where R²=H are identical with clausenamide and neoclausenamide which have been obtained from the plant extract. The new process makes it possible to prepare considerably larger amounts in a shorter time and in a less complex procedure, compared with the extraction process.

PREPARATION EXAMPLES

EXAMPLE 1

N-Methyl-N-phenacyl-cinnamamide

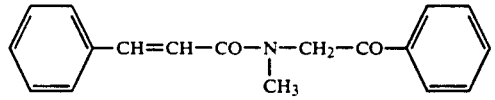

A chromium oxide solution is prepared by adding 9.0 g (0.09 mol) of chromium oxide to a mixture of 14.25 g (0.18 mol) of dry pyridine and 210 ml of methylene chloride. The mixture is subsequently stirred for 1 hour at room temperature, which gives a red solution. 4.2 g (0.015 mol) of N-methyl-N-(β-hydroxy-β-phenyl)-ethylcinnamamide in 40 ml of methylene chloride are added to this solution, and the mixture is stirred for 15 minutes. The reaction solution is rapidly applied to a short column (silica gel 25×2 cm), and the latter is washed with 200 ml of methylene chloride. The filtrate is evaporated down to dryness. This gives 3.4 g of a yellow solid which is recrystallized from benzene.

| Yield: | 3.1 g | M.p. °C.: | 141–142.5° C. |
| | 0.1 g | M.p. °C.: | 138–141° C. (from mother liquor) |

Empirical formula $C_{18}H_{17}NO_2$,
Elemental analysis calc. % =C 77.42, H 6.09, N 5.02; found % =C 77.44, H 6.12, N 4.90.

EXAMPLE 2

N-Methyl-N-(β-hydroxy-β-phenyl)-ethyl-3-phenyl-glycidamide

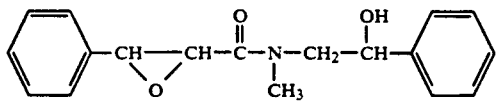

a) 35.7 g (0.2 mol) of methyl 3-phenylglycidate in 50 ml of methanol and 43.6 g (0.28 mol) of N-methyl-β-hydroxy-β-phenyl-ethylamine in 50 ml of methanol are each cooled to −16° C. and subsequently combined with the addition of 1.0 g of 4-dimethylaminopyridine.

The mixture is allowed to stand for 5 days at a temperature of −16° C., and a 20 ml portion of water is added each day, with stirring. After 5 days, the residue is filtered off and washed with ice-cold methanol until flocculation occurs. This gives a white solid.

Yield: 25.9 g (43.5% of theory). $R_f$: 0.35 (SiO$_2$ plate, mobile-phase system of chloroform/methanol 100:3).

M.p. °C.: 143°–146° C.

b) 2.6 g of a 25–28% strength methanolic solution of sodium methoxide are added to a solution of 33.2 g (0.22 mol) of N-methyl-β-hydroxy-β-phenylethylamine in 50 ml of methanol. The mixture is cooled to −16° C., and a cold solution (−16° C.) of 35.6 g (0.2 mol) of methyl 3-phenylglycidate in 50 ml of methanol is added. The solution is allowed to stand for 24 hours at −16° C. The residue is filtered off and then washed with ice-cold methanol and ether More product is obtained from the mother liquor. This gives a white solid.

Yield 27.5 g (46.3% of theory).
M.p. °C.: 150°–151° C.

EXAMPLE 3

N-Methyl-N-phenacyl-3-phenylglycidamide

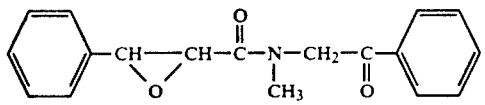

a) 2.4 g (0.0086 mol) of the compound of EXAMPLE 1 and 8.6 g (0.04 mol) of m-chloroperbenzoic acid are dissolved in 170 ml of chloroform, and the solution is allowed to stand at room temperature for 2 days. The residue is filtered off, and the filtrate is washed in succession with sodium sulphite solution (10% strength), sodium carbonate solution (10% strength) and water, and dried over anhydrous sodium sulphate. The solvent is removed, the residue is dissolved in 6 ml of benzene/dry ether (1:1), and the solution is cooled in a refrigerator. After unreacted starting material has been removed, the mixture is filtered. The oily residue is purified by chromatography, Yield: 1.25 g (49.2% of theory)

$^1$H-NMR (90 MHz, CDCl$_3$): δ = 3.09 (s) +3.21 (s, 3H, NCH$_3$); 3.49 (d) +3.88 (d, J=2.7 Hz, 1H); 4.04 (d) +4.15 (d, J=2.7 Hz, 1H); 4.82, 5.04 (AB, J=18 Hz) +4.96 (s, 2H); 7.30–7.8 (m, 8H); 8.01 (dd, J=1.8 Hz, 8 Hz) +8.06 (dd, J=2.7 Hz, 8 Hz, 2H).

b) 36 g of activated manganese dioxide are added to a vigorously stirred solution of 5.94 g (0.02 mol) of the compound of Example 2. The mixture is stirred for 1.5 hours until starting material is no longer detectable by thin-layer chromatography. The manganese dioxide is filtered off and washed with methylene chloride. The combined filtrates are first washed with 20 ml of a 15% strength sodium hydrogen sulphite solution and with 20 ml of a saturated sodium chloride solution, and dried over anhydrous sodium sulphate. This gives a viscous transparent residue which solidifies upon standing. Recrystallization gives white needles.

Yield: 4.42 g (75% of theory).
M.p. °C.: 76.5°–79° C.

After a second recrystallization, a melting point of 78.5°–80° C. is detected $^1$H-NMR (CDCl$_3$): δ = 3.12 (s) +3.26 (s); (3H, NCH$_3$); 3.52 (d) +3.85 (d, 1H, J=2 Hz); 4.07 (d), 4.19 (d, 1H, J=2 Hz); 4.88 (d); 5.10 (d); (2H, J=18 Hz, PhCOCH$_2$); 7.30–8.16 (m, 10H).

The compounds listed in Tables 1 and 2 below can be prepared analogously to the procedures of Examples 2 and 3.

TABLE 1

| Example no. | R$^2$ | M.p. °C. | Yield |
|---|---|---|---|
| 4 | m-Br | 145–146° C. | 38.4 g |
| 5 | m-Cl | 131–132° C. | 32.4 g |
| 6 | m-F | 134–135° C. | 29.5 g |
| 7 | p-F | 150–152° C. | 34.9 g |
| 8 | p-Br | 154–156° C. | 31.4 g |

TABLE 2

| Example no. | R$^2$ | M.p. °C. | Yield |
|---|---|---|---|
| 9 | m-Br | 117–119° C. | 71.3% |
| 10 | m-Cl | 85–87° C. | 67.1% |
| 11 | m-F | 81–83° C. | 72.9% |
| 12 | p-F | 99–101° C. | 85.7% |
| 13 | p-Br | 154–156° C. | 74.2% |

EXAMPLE 14 AND EXAMPLE 15

(±) 3(S*), 4(R*), 5(R*)-1-methyl-3-hydroxy-4-phenyl-5-benzoyl-pyrrolidin-2-one (14) and (±) 3(S*), 4(R*), 5(S*)-1-methyl-3-hydroxy-4-phenyl-5-benzoyl-pyrrolidin-2one (15)

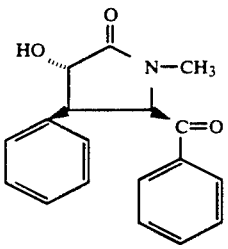

(14)

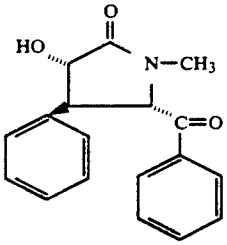

(15)

a) 490 mg (1.66 mmol) of the compound of Example 3 in 10 ml of tetrahydrofuran are added dropwise with stirring and cooling at −72° C. to a solution of 4 mmol of lithium diisopropylamide in 5 ml of tetrahydrofuran. The mixture is cooled for 4 hours and stirred until starting material is no longer detectable. After this, 100 ml of water are slowly added. Tetrahydrofuran is removed in vacuo. This gives 680 mg of a brown, semi-solid crude product which is purified by chromatography (Chromatotron). This gives the compound of Example 14, of a melting point of 193°-201° C. After recrystallization, the melting point is 208°-210° C. The product is identical with the compound which is obtained by oxidation of naturally occurring clausenamide. Furthermore, the melting points of the mixture are not reduced.

Empirical formula: $C_{18}H_{17}NO_3$

Elemental analysis: calc.: C 73.22, H 5.76, N 4.75, found : C 73.27, H 5.67, N 4.70.

$^1$H-NMR (CDCl$_3$): δ=2.92 (s, 3H, NCH$_3$); 3.92 (t, J=8.5 Hz, 1H, C$_4$H); 3.40 (br, s, 1H, exchangeable for D$_2$O); 4.93 (d, J=8.5 Hz, 1H, C$_3$-H); 5.50 (d, J=8.5 Hz, 1H, C$_5$-H); 7.04-7.84 (m, 10H, ArH).

Separation by chromatography also gives the compound of Example 15, having a melting point of 198°-200° C.

$^1$H-NMR (CDCl$_3$): δ=2.97 (s, 3H, NCH$_3$); 3.35 (t, J=7.2 Hz, 1H, C$_4$-H); 3.70 (br, s, 1H, exchangeable for D$_2$O); 4.58 (d, J=7.2 Hz, 1H, C$_3$-H); 5.18 (d, J=7.2 Hz, 1H, C$_5$-H); 7.04-7.84 (m, 10H, ArH).

from the mother liquor, a total yield of 80.6% of theory is obtained altogether.

Separation by column chromatography and recrystallization gives 1.55 g (17.6% of theory) of the compound of Example 14 of melting point 213°-215° C. and 4.8 g (54.5% of theory) of the compound of Example 15 of melting point 182°-183° C.

d) A solution of 0.168 g (4 mmol) of lithium hydroxide solution in 40 ml of water is cooled to 3° C., and 1.18 g (4 mmol) of the compound of Example 3 in 20 ml of methanol is added dropwise with stirring. The mixture is subsequently stirred for about 5 hours at 3° C. The mixture is placed overnight in a freezer, and this gives 0.96 g of a precipitated white solid which is filtered off from the solution, and a further 0.21 g from the filtrate.

Purification by chromatography and recrystallization gives 462 mg (39% of theory) of the compound of Example 14 of melting point 203°-205° C. and 357 mg (30% of theory) of the compound of Example 15.

The cyclization which gives the compounds of Examples 14 and 15 can also proceed under different reaction conditions, and these are listed in Table 3.

| Solvent | Base | Temp. °C. | Time h | Yield 14 + 15 | Ratio 14:15 |
|---|---|---|---|---|---|
| Dioxane | LDA (in hexane) | −65 | 5 | 21.4 | 1//2.5 |
| Benzene | BuLi (in hexane) | 10 | 3 | 22.7 | 1/2.6 |
| Benzene | NaH | 10 | 4 | 18.8 | 1/3 |
| t-BuOH | t-BuOLi | 25-30 | 2 | 23.2 | 1/3.6 |
| t-BuoOH | t-BuONa | 25-30 | 1.5 | 21.2 | 1/3.4 |
| t-BuOH | t-BuOK | 25-30 | 2/3 | 21.4 | 1/2.8 |
| CH$_3$OH | CH$_3$OLi | 2-4 | 3.5 | 83.4 | 1/1.9 |
| CH$_3$OH | CH$_3$OK | 2-4 | 4 | 75.5 | 1/2.1 |
| CH$_3$OH | LiOH.H$_2$O | 2-4 | 5 | 86.8 | 1/1.7 |
| CH$_3$OH | NaOH | 2-4 | 5 | 85.1 | 1/2 |
| CH$_3$OH | KOH | 2-4 | 5 | 80.1 | 1/1.9 |
| CH$_3$OH/H$_2$O | Me$_4$N$^+$OH$^-$ | 13 | 7 | 85 | 1/1.9 |
| CH$_2$Cl$_2$/H$_2$O | KOH | 15 | 12 | 77 | 1/2.1 |
| Et$_2$O/H$_2$O | KOH | 15 | 8 | 77 | 1/1.2 |
| Et$_2$O/THF/H$_2$O | LiOH | 6-8 | 2.5 | 80 | 1/1 |

The total yield of Example 14 and Example 15 together is 30% of theory, in a ratio of 1:2.

b) A solution of 2.95 g (10 mmol) of the compound of Example 3 in 70 ml of methanol is added to a stirred solution of sodium methoxide (prepared in situ from 1.15 g (5 mmol) of sodium and 100 ml of absolute methanol under a nitrogen atmosphere). The mixture is stirred for 30 minutes, acidified with 3.0 g of glacial acetic acid and then concentrated. The residue is dissolved in methylene chloride and separated by chromatography on a column (SiO$_2$). This gives 0.59 g (20% of theory) of the compound of Example 14 of melting point 210°-214° C. (recrystallized from ethyl acetate) and 1.59 g (53% of theory) of the compound of Example 15 of melting point 180°-182° C. (likewise recrystallized from ethyl acetate)

c) 8.8 g (28.8 mmol) of the compound of Example 3 are dissolved in 100 ml of methylene chloride, and 50 ml of a 1% strength tetramethylammonium hydroxide solution are added. The solution is stirred for 24 hours at room temperature. The organic phase is separated off, and the aqueous phase is extracted using methylene chloride. The organic phases are combined and washed with a saturated sodium bicarbonate solution and sodium chloride solution. Removal of the solvent gives 8.2 g of a solid. The latter is recrystallized from ethyl acetate, which gives 6.1 g of the compound of Example 15. Taking into consideration a further precipitation The examples listed in Table 4 are prepared analogously to the procedures of Examples 14 and 15:

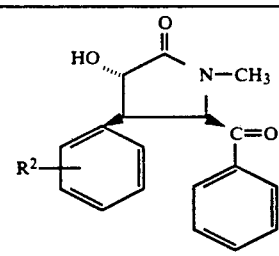

(14)

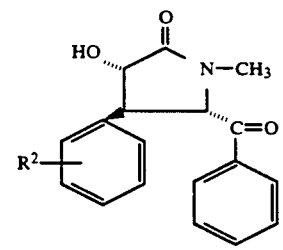

(15)

| Example no. | R$^2$ | Total yield (%) | M.p. °C. | IR |
|---|---|---|---|---|
| 16 | m-Br | 74.7 | 187-188 (cis) | 3250 (OH) 1700 (Ph—CO) 1670 (—NCO) |

-continued

| | | | | |
|---|---|---|---|---|
| 17 | m-Br | 74.7 | 166–168 (trans) | |
| 18 | m-Cl | 74.8 | 179–180 (cis) | 3240 (OH) 1680 (N—CO) (Ph—CO) |
| 19 | m-Cl | 74.8 | 160–162 (trans) | |
| 20 | m-F | 73 | 178–180 (cis) | 3300 (OH) 1670 (—NCO) 1700 (Ph—CO) |
| 21 | m-F | 73 | 155–157 (trans) | |
| 22 | p-F | 74.6 | 180–183 (cis) | 3250 (OH) 1675 (—NCO) 1690 (Ph—CO) |
| 23 | p-F | 74.6 | 157–159 (trans) | |
| 24 | p-Br | 76.6 | 173–175 (cis) | 3250 (OH) 1675 (—NCO) 1695 (Ph—CO) |
| 25 | p-Br | 76.6 | 145–147 (trans) | |

EXAMPLE 26

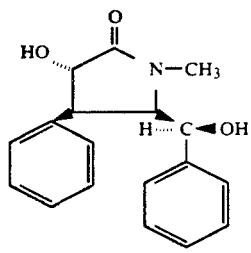

Clausenamide 15 mg (0.4 mmol) of sodium borohydride are added dropwise with stirring to a solution of 74 mg (0.25 mmol) of the compound of Example 14 in 10 ml of dry methanol. The mixture is stirred (for 40 minutes) until starting material is no longer detectable by thin-layer chromatography. The methanol is removed in vacuo, and the residue is acidified with dilute (5% strength) hydrochloric acid to establish a pH of 5–6. The residue is filtered off. More white solid is obtained from the methylene chloride extract of the acid aqueous phase. L The white solid is present in an amount of 62 mg (83.7% of theory) and has a melting point of 237°–239° C. After recrystallization, the melting point is at 244°–246° C. The melting point is not reduced if the synthetic product is mixed with the naturally obtained product.

Empirical formula: $C_{18}H_{19}NO_3$

Elemental analysis: calc.: C 72.70, H 6.44, N 4.71; found: C 72.57, H 6.46, N 4.50.

$^1$H-NMR (DMSO-d, 90 MHz): $\delta = 3.05$ (s, 3H, $NCH_3$); 3.60 (m, 1H, $C_4$-H); 3.88 (m, 1H, $C_3$-H); 4.32 (m, 1H, $C_5$-H); 4.67 (d, 1H, J=3 Hz, $C_7$-H); 5.42 (m, 1H, OH); 6.55–7.25 (m, 10H, ArH).

The compounds listed in Table 5 are prepared analogously to the procedure for Example 26:

TABLE 5

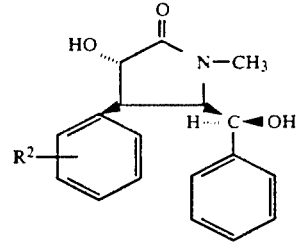

| Example no. | $R^2$ | M.p. °C | Yield | IR |
|---|---|---|---|---|
| 27 | m-Br | 215–217 | 85 | 1685 (amide) |
| 28 | m-Cl | 214–216 | 74 | 1665 (amide) |
| 29 | p-F | 251–253 | 75 | 1680 (amide) |
| 30 | m-F | 225–227 | 84 | 1675 (amide) |
| 31 | p-Br | 246–248 | 84 | 1660 (amide) |

EXAMPLE 32

(±) 3(S*), 4(R*), 5(S*)-1-methyl-3-o-tetrahydropyranyl-4-phenyl-5-benzoyl-pyrrolidin-2-one

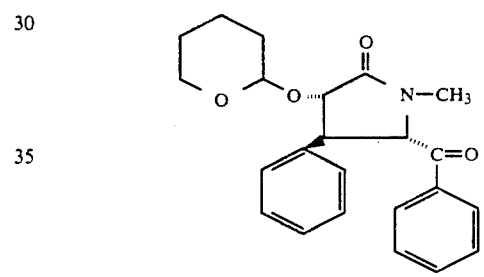

0.89 g (3 mmol) of the compound of Example 15 are dissolved in 35 ml of methylene chloride, and the solution is then reacted with 760 mg of 2,3-dihydropyran and 75 ml of pyridinium p-toluenesulphonate. The reaction solution is stirred overnight at room temperature. After this, 15 ml of methylene chloride are added, and the solution is washed with a saturated sodium chloride solution and dried over anhydrous magnesium sulphate. Removal of the solvent gives 1.6 g of a white solid. Purification by chromatography gives 1.05 g (92% of theory) of the title compound of melting point 165°–168° C. It is recrystallized from methylene chloride/diethyl ether. The crystals have a melting point of 173°–175° C.

Empirical formula: $C_{23}H_{25}NO_4$

Elemental analysis: calc.: C 72.80, H 6.64, N 3.69; found: C 72.97, H 6.66, N 3.73.

$^1$H-NMR (CDCl$_3$, 90 MHz): $\delta = 1.20$–2.0 (m, 6H); 2.93 (s, 3H, $NCH_3$); 3.10–3.48 (m, 3H); 4.46 +4.64 (d+d, 1H, J=6.3 Hz, $C_3$-H); 4.97 +4.95 (d+d, 1H, J=5.5 Hz, $C_5$-H); 5.17+4.10 (m+m, 1H); 7.10–7.70 (m, 10H, ArH).

EXAMPLE 33 AND EXAMPLE 34

(±) 3(S*), 4(R*), 5(S*),
7(R*)-1-methyl-3-hydroxy-4-phenyl-5-(α-hydroxyben-zyl)pyrrolidin-2-one (neoclausenamide)

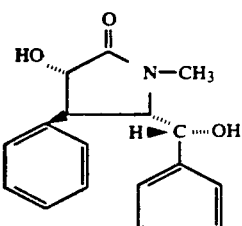
(38)

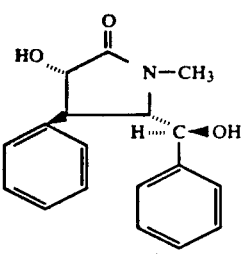
(39)

Reduction of lithium tri-sec-butyl-borohydride (a) 100 mg of the compound of Example 15 in 2 ml of dry tetrahydrofuran are cooled to 10° C., and 2 ml (2 mmol) of a lithium tri-sec-butyl-borohydride/tetrahydrofuran solution are added. The reaction solution is stirred for 1 hour at −10° C. After this, 1 ml of 30% strength hydrogen peroxide solution and 1 ml of 2 N sodium hydroxide solution are added. The mixture is extracted 3 times with 10 ml portions of methylene chloride. The extracts are washed with saturated sodium bicarbonate solution and with water and subsequently dried over dry sodium sulphate. The solvent is evaporated until the product is nearly dry. The mixture is subsequently treated with 2 ml of diethyl ether This gives 91 mg of a white solid.

Thin-layer chromatography shows the existence of 2 products having the $R_f$ values 0.23 and 0.35 (silica gel plate, ethyl acetate), which can be assigned to neoclausenamide (Example 33) and to the isomer (Example 34). The thin-layer chromatogram and the shift of the signals of the —N—CH$_3$ group in the $^1$H-NMR (δ=3.15; 2.89) makes it possible to determine the ratio of the product formation of the Examples 33 and 34 as 3:1.

(b) A solution of 379 mg (1.0 mmol) of the compound of Example 32 in 8 ml of tetrahydrofuran is treated with 3 ml (3 mmol) of lithium tri-sec-butyl-borohydride in tetrahydrofuran at −15° C. The reaction solution is stirred for 40 minutes at −10° C. to −15° C. After this, 5 ml of water are added, and the solution is acidified with 1 ml of 3.7N sulphuric acid. The mixture is stirred for 5 hours at room temperature and extracted with 50 ml of chloroform. The chloroform solution is washed in succession with 2N sodium hydroxide solution, sodium bicarbonate solution and saturated sodium chloride solution until the solution is neutral. The solution is dried, and the solvent is removed. The residue is recrystallized in the system ethanol/water (1:1) which contains 1 drop of 3.7N sulphuric acid. This gives 240 mg (51% of theory) of a solid of melting point 209°–212° C.

(melting point of naturally occurring neoclausenamide: 205°–206° C.).

$^1$H-NMR (CDCl$_3$, 90 MHz): δ=2.0 (br.s, 2H); 3.08 (s, 3H, NCH$_3$); 3.15 (t, 1H, J=3 Hz, C$_4$-H); 3.74 (t, 1H, J=3 Hz, C$_5$-H); 4.13 (d, 1H, J=3 Hz, C$_3$-H); 5.17 (d, 1H, J=3 Hz, C$_7$-H); 6.64–7.29 (m, 10H, ArH).

The results of the reduction of the compounds of Examples 15 and 32 under different reaction conditions are documented by the Examples listed in Table 6.

TABLE 6

| Starting compound | Solvent | Temp. (°C.) | Ratio (33)/(34) | Yield (%) |
|---|---|---|---|---|
| 15 | MeOH | RT | 1.2/1 | 60 |
| 32 | MeOH | RT | 10/1 | 54 |
| 15 | THF | RT | 1/1 | 54 |
| 32 | THF | RT | 10/1 | 41 |
| 15 | CH$_2$Cl$_2$ | 0–5 | 1/2 | 91 |
| 32 | CH$_2$Cl$_2$ | 0–5 | 8/1 | 77 |
| 15 | DME | 0 | 1/1.2 | |
| 15 | THF | −15 | 2.8/1 | 80–90 |
| 32 | THF | −15 | 10/1 | 81 |
| 15 | i-PrOH | 80 | 1/20 | 80–90 |
| 32 | i-PrOH | 80 | 1/1 | 57 |
| 15 | Et$_2$O | RT | 1.5/1 | 70 |

Experimental part, appendix
DME = dimethoxyethane
LDA = lithium diisopropylamide
tBuOH = tert.butanol
THF = tetrahydrofuran
CH$_2$Cl$_2$ = methylene chloride
i-PrOH = isopropanol
MeOH = methanol

What is claimed is:
1. A process for the preparation of a compound of the formula (I):

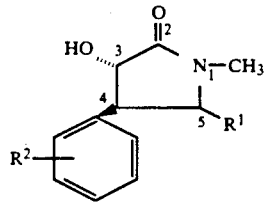
(I)

in which

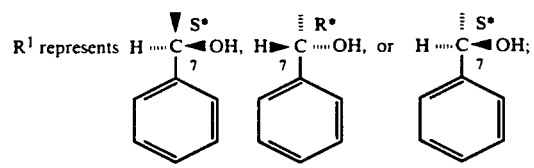

$R^1$ represents and $R^2$ represents hydrogen, fluorine, chlorine or bromine;

said process comprising cyclizing a compound of the formula (II):

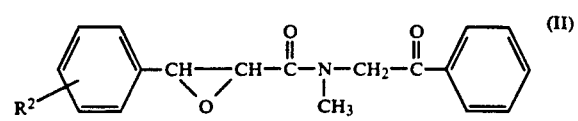
(II)

in an inert organic solvent and in the presence of a base to form two isomers of the formulae (III) and (IV):

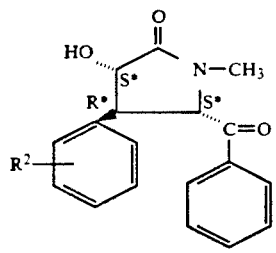
(III)

and

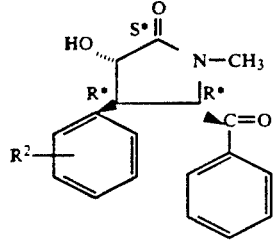
(IV)

and then either:
(a) reducing the isomer of the formula (IV) stereospecifically to form the compound of the formula (I) wherein R¹ represents:

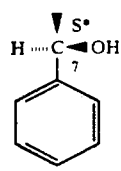

or
(b) reducing the isomer of the formula (III) to form the compound of the formula (I) wherein R¹ represents:

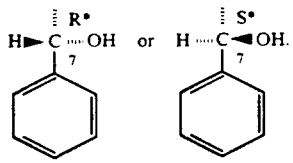

2. Process according to claim 1, wherein the inert organic solvents for the cyclization are ethers, alcohols, halogenated hydrocarbons, or mixtures thereof.

3. Process according to claim 1 wherein the bases employed in the cyclization are sodium ethoxide, sodium methoxide, potassium butoxide, sodium butoxide, lithium butoxide, lithium hydroxide, sodium hydroxide, potassium hydroxide, sodium hydride, lithium diisopropylamide, butyllithium or non-toxic quaternary ammonium hydroxides.

4. Process according to claim 1, wherein the cyclization is carried out under the conditions of a 2-phase-transfer reaction.

5. Process according to claim 1, wherein the reduction of the keto function to the hydroxyl function is carried out with sodium borohydride, zinc borohydride, lithium tri-sec-butyl-borohydride or aluminum propoxide.

6. The process according to claim 3, wherein the non-toxic quaternary ammonium hydroxide base is tetramethylammonium hydroxide.

7. A process for the preparation of a compound of the formula (I):

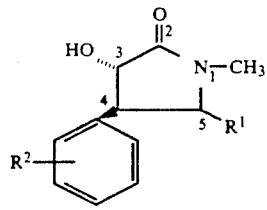
(I)

wherein
R¹ represents

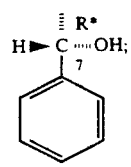

and
R² represents hydrogen, fluorine, chlorine or bromine;
said process comprising cyclizing a compound of the formula (II)

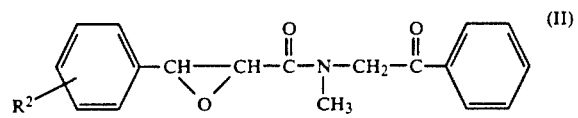
(II)

in an inert organic solvent in the presence of a base to form an isomer of the formula (III):

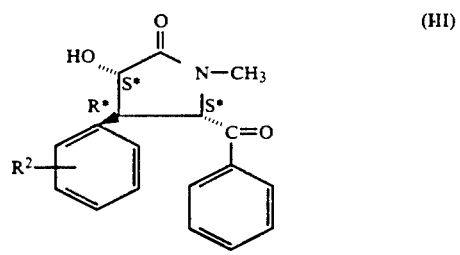
(III)

and reacting the isomer of the formula (III) with 2,3-dihydropyran to form a compound of the formula (V):

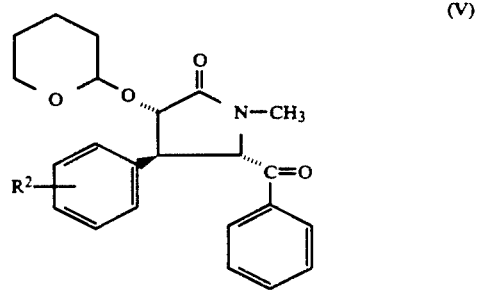
(V)

and reducing the compound of the formula (V) stereospecifically.

8. Process according to claim 7, wherein the etherification with 2,3-dihydropyran is carried out in methylene chloride in the presence of pyridinium p-toluenesulphonate.

9. Process according to claim 7, wherein the inert organic solvents for the cyclization are ethers, alcohols, halogenated hydrocarbons, or mixtures thereof.

10. Process according to claim 7, wherein the bases employed in the cyclization are sodium ethoxide, sodium methoxide, potassium butoxide, sodium butoxide, lithium butoxide, lithium hydroxide, sodium hydroxide, potassium hydroxide, sodium hydride, lithium diisopropylamide, butyllithium or non-toxic quaternary ammonium hydroxides.

11. Process according to claim 7, wherein the cyclization is carried out under the conditions of a 2-phase transfer reaction.

12. Process according to claim 7, wherein the reduction of the keto function to the hydroxyl function is carried out with sodium borohydride, zinc borohydride, lithium tri-secbutylborohydride or aluminum propoxide.

13. The process according to claim 7, wherein the non-toxic quaternary ammonium hydroxide base is tertramethylammonium hydroxide.

* * * * *

UNITED STATES PATENT AND TRADEMARK OFFICE
CERTIFICATE OF CORRECTION

PATENT NO. : 5,132,433

DATED : July 21, 1992

INVENTOR(S) : Huang et al.

It is certified that error appears in the above-identified patent and that said Letters Patent is hereby corrected as shown below:

Col. 22, line 9    Delete " secbutylborohydride " and substitute -- sec-butylborohydride --

Col. 22, line 11   Delete " claim 7 " and substitute -- claim 10 --

Col. 22, lines 12-13   Delete " tertramethylammonium " and substitute -- tetramethylammonium --

Signed and Sealed this

Twenty-first Day of December, 1993

Attest:

BRUCE LEHMAN

*Attesting Officer*    Commissioner of Patents and Trademarks